United States Patent
Kordova

(10) Patent No.: US 6,635,765 B2
(45) Date of Patent: Oct. 21, 2003

(54) PROCESSES FOR PREPARING TORSEMIDE INTERMEDIATE

(75) Inventor: Marco Kordova, Kfar Saba (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 0 days.

(21) Appl. No.: 09/812,762

(22) Filed: Mar. 20, 2001

(65) Prior Publication Data

US 2002/0019537 A1 Feb. 14, 2002

Related U.S. Application Data

(60) Provisional application No. 60/190,650, filed on Mar. 20, 2000, and provisional application No. 60/211,510, filed on Jun. 14, 2000.

(51) Int. Cl.$^7$ ............................................. C07D 213/71
(52) U.S. Cl. ...................................................... 546/293
(58) Field of Search ......................................... 546/293

(56) References Cited

U.S. PATENT DOCUMENTS

| | | | |
|---|---|---|---|
| 2,516,025 | A | 7/1950 | Sonnemann |
| 3,674,794 | A | 7/1972 | Mizzoni et al. |
| 3,787,573 | A | 1/1974 | Mizzoni et al. |
| 3,819,639 | A | 6/1974 | Delarge et al. |
| 3,824,241 | A | 7/1974 | Mizzoni et al. |
| 3,904,636 | A | 9/1975 | Delarge et al. |
| 4,018,929 | A | 4/1977 | Delarge et al. |
| 4,042,693 | A | 8/1977 | Delarge et al. |
| 4,055,650 | A | 10/1977 | Delarge et al. |
| 4,244,950 | A | 1/1981 | De Ridder et al. |
| RE30,633 | E | 6/1981 | Delarge et al. |
| 4,743,693 | A | 5/1988 | Topfmeier et al. |
| 4,822,807 | A | 4/1989 | Topfmeier et al. |
| 4,861,786 | A | 8/1989 | Demmer et al. |
| RE34,580 | E | 4/1994 | Topfmeier et al. |
| RE34,672 | E | 7/1994 | Topfmeier et al. |
| 5,459,138 | A | 10/1995 | Pirotte et al. |
| 5,914,336 | A | 6/1999 | Dreckmann-Behrendt |

FOREIGN PATENT DOCUMENTS

| | | |
|---|---|---|
| CA | 1051888 | 4/1979 |
| DE | 25 14 334 | 4/1975 |
| EP | 2054142 | 6/1971 |
| EP | 003 383 | 1/1979 |
| EP | 0 618 209 B1 | 3/1994 |
| EP | 0 618 209 A1 | 3/1994 |

OTHER PUBLICATIONS

Thunus Synthesis of some 4–(piperzinyl) etc CA 85:21295 (1975).*

The Merck Index, Twelfth Edition, Published by Merck Research Laboratories, 1996, p. 1648.

DeLarge, J., "Chemistry and Pharmacological Properties of the Pyridine–3–Sulfonylurea Derivative Torasemide", Arzneimittel Forschung: Drug Research, Jan. 1988, vol. 38, No. 1a, pp. 144–149.

DuPont, P. et al. "Structure d'une Seconde Variétéde la Torasémide," Acta Cryst. (1978). B34, pp. 2659–2662.

DuPont, P., Structure Cristalline et Moléculaire d'un Diurétique Dérivéde l'Alkyl–1 [(Phénylamino–4pyridyl–3) sulfonyl]–3 Urée: la Torasémide ($C_{15}H_{20}N_4SO_3$), Acta Cryst. (1978). B34, pp. 1304–1310.

3–(Alkylamino)–4H–pyrido[4,3–e]–1,2,4–thiadiazine 1,1–Dioxides as Poweful Inhibitors of Insulin Release from Rat Pancreatic B–Cells: A New Class of Potassium Channel Openers?, Journal of Medicinal Chemistry, vol. 36, No. 21, Oct. 15, 1993, pp. 3211–3213.

Design, Synthesis and Biological Activity of a Series of Torasemide Derivatives, Potent Blockers of the Na+2Cl–K+ Co–transporter: In–vitro Study, Journal of Pharmacy and Pharmacology, vol. 44, No. 7, Jul., 1992, pp. 589–593.

**J. Delarge, Synthese de nouvelles substances anti–inflammatoires non steroidiques, Memoires de I'Academie Royale de Medecine de Belgique, vol. 47, No, 33, 1974.

Synthesis and Structural Studies of a New Class of Heterocyclic Compounds: 1,2,4–Pyridothiadiazine 1,1–Dioxides, Pyridyl Analogous of 1,2,4–Benzothiadiazine 1,1–Dioxides, de Tullio, et al., Tetrahedron, vol. 51, No. 11, pp. 3221–3234, 1995.

84:59218—Chemical Abstracts, vol. 84, No. 9, Mar., 1976.
90:80729—Chemical Abstracts, vol. 90, No. 11, Mar., 1979.
92:128730—Chemical Abstracts, vol. 92, No. 15, Apr. 1980.
117:142865—Chemical Abstracts, vol. 117, No. 15, Oct. 1992.

**J. Delarge, Nouveaux anti–inflammatories derives de la pyridine, Annales pharmaceutiques francaises, No. 31, Nov. 6, 1973, pp. 467–474.

J. Delarge et al., Une nouvelle classe de diuretiques [high ceiling], derives de l'alkyl–1 [(phenylamino–4 pyridyl–3) sulfonyl]3 uree, Annales pharmaceutiques francaises, 1978, No. 7–8, pp. 369–380.

**Nobuo Kondo et al., Chemical Structure and Physico–chemical Properties of Torasemide, Iyakuhin Kenkyu, vo. 25, No. 9, 1994; pp. 735–749.

**J. Delarge, Synthese de quelques derives piperazinyl–4–pyridine substitues en 3, Annales pharmaceutiques francaises, 33, No. 10, 1975, pp. 487–494.

**E. Koenigs et al., Uber die sulfurierung des γ–amino–und γ–oxy–pyridins, Berichte Der Deutschen Chemischen Gesellschaft, 1924, pp 2080–2082.

* cited by examiner

Primary Examiner—Patricia L. Morris
(74) Attorney, Agent, or Firm—Kenyon & Kenyon

(57) ABSTRACT

The present invention relates to new methods for the synthesis of torsemide and the torsemide synthetic intermediate, (3-sulfonylchloride-4-chloro)pyridine.

21 Claims, No Drawings

PROCESSES FOR PREPARING TORSEMIDE INTERMEDIATE

CROSS-REFERENCE TO RELATED INVENTIONS

This application claims the benefit of provisional application Ser. No. 60/190,650, filed Mar. 20, 2000; and No. 60/211,510, filed Jun. 14, 2000, both of which are incorporated herein by reference.

FIELD OF THE INVENTION

The present invention relates to new processes for making the torsemide intermediate, (3-sulfonamide-4-chloro) pyridine. The present invention relates to new processes for making torsemide.

BACKGROUND OF THE INVENTION

1-Isopropyl-3-[(4-m-toluidino-3-pyridyl) sulfonyl] urea, which has the chemical structure

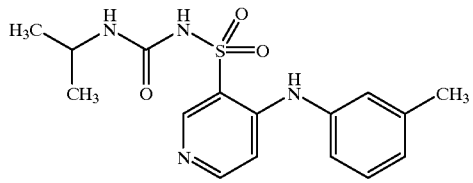

is approved, under the trademark DEMADEX®, by the U.S. Food and Drug Administration for the treatment of hypertension and edema associated with congestive heart failure, renal disease, or hepatic disease. The USAN approved generic name for this compound is torsemide, although this compound is also referred to as "torasemide" in the art. Torsemide is a loop diuretic that has been found to be particularly effective for the treatment of edema associated with chronic renal failure.

The synthesis of torsemide, torsemide intermediates and torsemide derivatives are described in the following references: Delarge, *Ann. Pharm. Fr.* 31, 467–474 (1973); Delarge, *Mem. Acad. R. Med. Belg.* 47(3), 131–210 (1974); E. Koenigs et al, *Chem. Ber.* 57, 2080–2082 (1924); L. Thunus, *Ann. Pharm. Fr.* 33, 487–494 (1975); Kondo, et al. *Iyakuhin Kenkyu*, 25(9), 734–50 (1994); EP 618,209; and U.S. Pat. Nos. 2,516,025; 6,674,794; 4,244,950 and Re. 30,633; all of which are incorporated herein by reference.

A process for the preparation of the torsemide intermediates (3-sulfonamide-4-chloro)pyridine, 3-sulfomamide-4-(3'-methylphenyl) aminopyridine and torsemide is described in Scheme 1.

Scheme 1

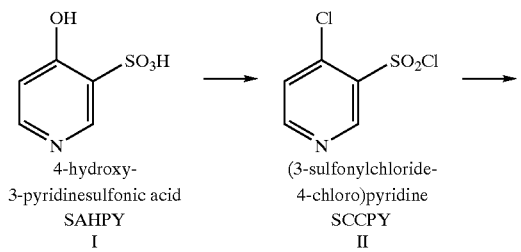

4-hydroxy-3-pyridinesulfonic acid
SAHPY
I (3-sulfonylchloride-4-chloro)pyridine
SCCPY
II -continued

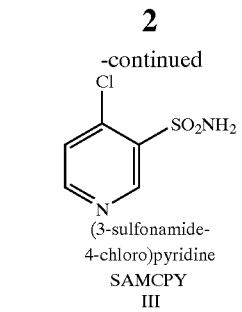

(3-sulfonamide-4-chloro)pyridine
SAMCPY
III

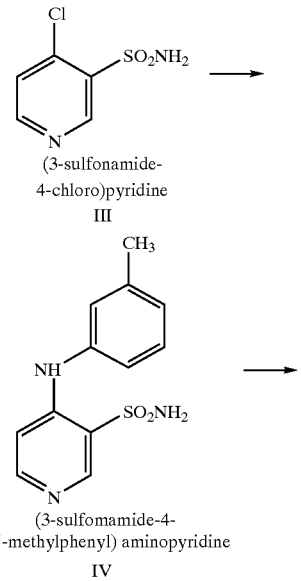

(3-sulfonamide-4-chloro)pyridine
III (3-sulfomamide-4-(3'-methylphenyl) aminopyridine
IV

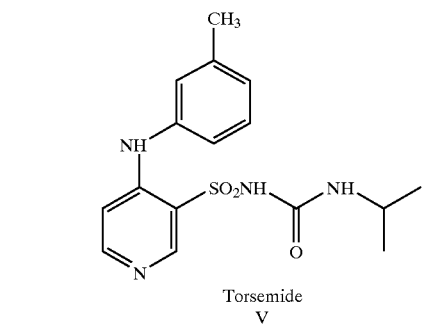

Torsemide
V

In known processes where (3-sulfonamide-4-chloro) pyridine is made from (3-sulfonylchloride-4-chloro) pyridine (SCCPY→SAMOPY), the reaction is performed in a polar solvent, such as, acetone or dioxane, or in melted reagent as a solvent in the presence of large excess of ammonium hydroxide. By these known processes, (3-sulfonylchloride-4-chloro)pyridine (SCCPY), is added dropwise into an aqueous solution of ammonium hydroxide. The dropwise addition of (3-sulfonylchloride-4-chloro) pyridine into an excess of ammonium hydroxide is a method to try to minimize the condensation of (3-sulfonylchloride-4-chloro)pyridine with the newly formed desired product, (3-sulfonamide-4-chloro)pyridine (SAMCPY). These harsh reaction conditions necessitate a great effort in purifying the resulting product as well as creating environmental waste disposal issues associated with neutralizing and disposing of large volumes of concentrated basic solutions. The highly basic conditions make the procedures employing a large excess of base very costly. Thus in such conditions the desired (3-sulfonamide-4-chloro)pyridine is made in low yields, of about 50%, and is isolated with a high percentage of impurities thus requiring additional purification steps. It is desirable to have a process for making (3-sulfonamide-4-chloro)pyridine without the condensation of (3-sulfonylchloride-4-chloro)pyridine and (3-sulfonamide-4-chloro)pyridine. It is desirable to have a process for making (3-sulfonamide-4-chloro)pyridine which gives high yields and high purity which is suitable for large scale manufacturing procedures.

In known processes where torsemide is made from 3-sulfonamide-4-(3'-methylphenyl) aminopyridine, the reaction may be performed in dioxane or dichloromethane in the presence of triethyl amine and isopropyl-isocyanate. Under such conditions the desired torsemide is made in low yields and is isolated with a high percentage of impurities thus requiring additional purification steps. The yields of these processes are low, highly variable and not are not suitable for large scale manufacturing processes. It is therefore desirable to have processes for making torsemide which gives high yields and high purity which uses solvents that are suitable for large scale manufacturing procedures.

SUMMARY OF THE INVENTION

The present invention relates to s process for making a compound of the formula:

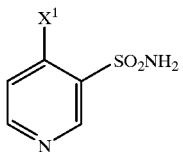

comprising the steps of: (a) adding a compound of the formula

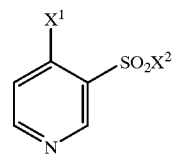

to an organic solvent; (b) adding ammonium hydroxide in an amount of about 1.75 to about 2.25 mole equivalents; and (c) isolating the compound of the formula:

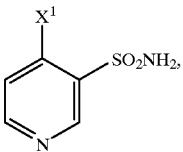

wherein $X^1$ and $X^2$ are each independently chloro, fluoro or bromo.

In a preferred embodiment of the present invention, $X^1$ and $X^2$ are both chloro.

In another preferred embodiment of the present invention, the organic solvent is selected from the group consisting of t-butyl-methyl ether, toluene, acetonitrile, methyl-isobutyl ketone, ethyl-methyl ketone, acetone, benzene, xylene, ethanol and isopropanol.

In another embodiment of the present intention, the organic solvent is t-butyl-methyl ether.

In another embodiment of the present intention, the ammonia is an aqueous solution.

In another embodiment of the present intention, the ammonia is added to the solution of step (a).

In another embodiment of the present invention, the ammonia is added in an amount of about 1.75 to about 2.25 mole equivalents.

The present invention also relates to a process for making (3-sulfonamide-4-chloro)-pyridine comprising the steps of: (a) adding (3-sulfonylchloride-4-chloro)pyridine to an organic solvent; (b) adding ammonia; and isolating (3-sulfonamide-4-chloro)pyridine.

In a preferred embodiment of the present invention, the organic solvent is selected from the group consisting of t-butyl-methyl ether, toluene, acetonitrile, methyl isobutyl ketone, ethyl methyl ketone, acetone, benzene, xylene, ethanol and isopropanol. In another embodiment of the present intention, the organic solvent is t-butyl methyl ether. In another embodiment of the present intention, the ammonia is added as an aqueous solution. In another embodiment of the present intention, the ammonia is added to the solution of step (a). In another embodiment of the present invention, the ammonia is added in an amount of about 1.75 to about 2.25 mole equivalents.

The present invention also relates to a process for preparing torsemide comprising the step of reacting 3-sulfonylamide-4(3'-methylphenyl)-aminopyridine with isopropyl isocyanate in the presence of triethyl amine in a solvent selected from the group consisting of acetonitrile, toluene, acetone, ethyl acetate and butyl acetate, and mixtures thereof. In a preferred embodiment of the present invention, the solvent is acetone. In another preferred embodiment of the present invention, the solvent is acetonitrile.

DETAILED DESCRIPTION OF THE INVENTION

The present invention relates to new processes for making the torsemide intermediate (3-sulfonamide-4-chloro) pyridine. The methods of the present invention provide for the synthesis of (3-sulfonamide-4-chloro)pyridine in substantially higher yields and higher purity than previously reported. The intermediate (3-sulfonylchloride-4-chloro) pyridine may be prepared from 4-hydroxy-3-pyridine sulfonic acid by methods known in the art, including methods disclosed in Canadian Patent No.: 1,051,888, and *J. Med. Chem.*, 36 3211–3213, 1993, the content of both are incorporated herein by reference.

By the methods of the present invention, a compound of formula II', wherein $X^1$ and $X^2$ are each independently chloro, fluoro or bromo; is added to a suitable organic solvent (Scheme II). Preferably, $X^1$ and $X^2$ are chloro. Suitable organic solvents include acetonitrile, ethers, such as, t-butyl methyl ether (MTBE), alcohols, such as, ethanol and isopropanol, ketones, such as, methyl-isobutyl ketone (MIBK), ethyl methyl ketone and acetone; and substituted or unsubstituted aromatics, such as, benzene and xylene. A preferred solvent is t-butyl methyl ether. Ammonia is then added to the mixture which may cause the mixture to rise in temperature. Preferably, about 2 mole equivalents of ammonia are added. Ammonia may be added in the form of gaseous ammonia or ammonium hydroxide, and more preferably as an aqueous solution of ammonium hydroxide. Preferably ammonium hydroxide is added as a 25% aqueous solution. The solution is cooled to room temperature and stirred until the reaction is substantially complete, e.g., 1 to 1.5 hours, preferably one hour. Completion of the reaction may be monitored by pH; which is indicated when the pH stops decreasing and stabilizes. The pH of the solution is adjusted to about 8±0.1 by the addition of ammonium hydroxide to induce the precipitation of crystals of the compound of formula III'. The compound of the formula III' wherein $X^1$ is chloro, fluoro or bromo; is isolated upon filtering the solution followed by drying (Scheme I1). Preferably $X^1$ is chloro.

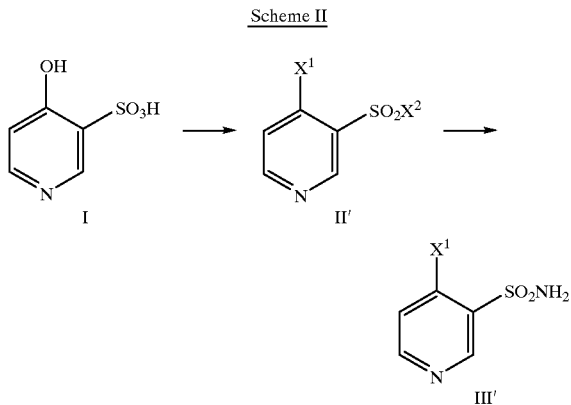

Scheme II

In an embodiment of the present invention, a compound of the formula II, (3-sulfonylchloride-4-chloro)pyridine, is added to an organic solvent. Suitable organic solvents include acetonitrile, ethers, such as, t-butyl methyl ether (MTBE), alcohols, such as, ethanol and isopropanol, ketones, such as, methyl-isobutyl ketone (MIBK), ethyl methyl ketone and acetone; and substituted or unsubstituted aromatics, such as, benzene and xylene. A preferred solvent is t-butyl methyl ether. Approximately 1.75 to about 2.25 mole equivalents of ammonia is then added to the solution. Preferably, about 2.15 mole equivalents of ammonia are added. Ammonia may be added in the form of gaseous ammonia or ammonium hydroxide, and more preferably as an aqueous solution of ammonium hydroxide. Preferably ammonium hydroxide is added as a 25% aqueous solution. Addition of the ammonia may cause the temperature of the solution to rise. The solution is cooled to room temperature and stirred until the reaction is substantially complete, e.g., 1 to 1.5 hours, preferably one hour. Completion of the reaction may be monitored by pH; which is indicated when the pH stops decreasing and stabilizes. The pH of the solution is adjusted to about 8±1 by the addition of ammonium hydroxide to induce the precipitation of crystals of (3-sulfonamide-4-chloro)pyridine, the compound of the formula III. (3-Sulfonamide-4-chloro)pyridine, the compound of the formula III, is isolated upon filtering the solution followed by drying. The (3-sulfonamide-4-chloro)pyridine is isolated in a high yield of about 74%. By the present methods, the (3-sulfonamide-4-chloro)pyridine is isolated in an unexpectedly high purity of about 93% to about 97%.

Thus, surprisingly the present methods provide processes for making high purity (3-sulfonamide-4-chloro)pyridine while using a high concentration of the starting material, (3-sulfonylchloride-4-chloro)pyridine. In contrast to the known methods, the present methods surprisingly yield (3-sulfonamide-4-chloro)pyridine substantially free of by-products resulting from the condensation of the starting material and product, (3-sulfonylchloride-4-chloro)pyridine and (3-sulfonamide-4-chloro)pyridine, which is observed in the known processes.

Scheme III

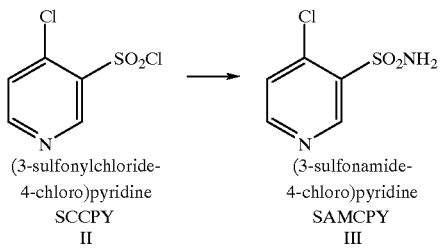

(3-sulfonylchloride-4-chloro)pyridine
SCCPY
II (3-sulfonamide-4-chloro)pyridine
SAMCPY
III The present method thus provides a new process with high yields and high purity which is suitable for use in large scale reactions. The high purity also reduces the need for additional purification steps.

The present invention also relates to a new process for making torsemide from 3-sulfonamide-4-(3'-methylphenyl) aminopyridine. 3-Sulfomamide-4-(3'-methylphenyl) aminopyridine may be prepared from (3-sulfonamide-4-chloro) pyridine by methods known in the art, including methods disclosed in U.S. Pat. No. 3,904,636, the content of which is incorporated herein by reference.

By the processes of the present invention, a compound of the formula IV, 3-sulfomamide-4-(3'-methylphenyl) aminopyridine, is added to triethylamine (TEA) and an organic solvent (Scheme IV). Suitable solvents are acetonitrile, toluene, acetone, ethyl acetate and butyl acetate, and mixtures thereof. Preferred solvents are acetonitrile and acetone. A more preferred solvent is acetonitrile. Isopropyl isocyanate (IPIC) is then added dropwise to the solution and the solution is heated to about 40° C. The resulting mixture is then stirred at about 38° C. to about 42° C. until there is complete dissolution of all the reactants, about 45 to 90 minutes. The mixture is then cooled to room temperature and stirred for a suitable time, about 1.5 to about 2.5 hours and preferably about 2 hours. The pH of the mixture is then adjusted to about 4.3±0.3, preferably to 4.3 with increasing the temperature to about 35° C. The pH may be lowered with hydrochloric acid. The mixture is cooled room temperature, followed by filtration and washing. The wet crude product is triturated, followed by drying to yield crude torsemide. The yield of isolated crude torsemide is about 81.5%. The purity of the isolated crude torsemide is about 98% to about 99.9% which is a substantial improvement over the methods known in the art.

Scheme IV

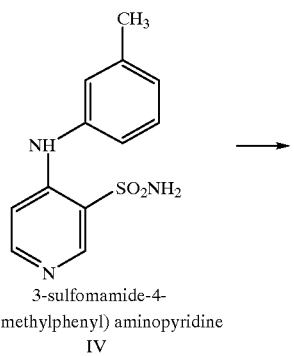

3-sulfomamide-4-(3'-methylphenyl) aminopyridine
IV

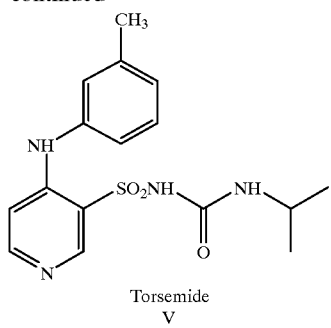

Torsemide
V

EXAMPLES

The present invention will now be further explained in the following example. However, the present invention should not be construed as limited thereby. One of ordinary skill in the art will understand how to vary the exemplified preparations to obtain the desired results.

Example 1

Synthesis of (3-sulfonamide-4-chloro)pyridine

In a 100 mL three necked flask equipped with magnetic stirrer, condenser, thermometer and dropping funnel (3-sulfonylchloride-4-chloro)pyridine (10 g, 1 eq., 46.7 mmoles) was suspended in MTBE (30 mL) at room temperature. Ammonium hydroxide, 25% solution (13.5 mL, 2.13 eq.) was dropped into the suspension in a rate such that the temperature is allowed to increase to about 22 to abut 26° C., this temperature was maintained until all the ammonium hydroxide was added. The suspension was then to cooled to room temperature and was stirred for one hour. The pH of the suspension was adjusted to 8±0.1 by the addition of a few drops of ammonium hydroxide, 25% solution. The suspension was filtered and washed with water (2×10 mL) and the wet product (~8 g) dried at 40° C., under the 1 mm Hg vacuum. (3-Sulfonamide-4-chloro)pyridine was isolated in 74.4% yield, 6.7 g.

Example 2

Synthesis of Torsemide

A 100 mL three necked flask, equipped with mechanical stirrer, thermometer and a condenser was charged with acetonitrile (15 mL), 3-sulfomamide-4-(3'-methylphenyl) aminopyridine (5 g), and triethyl amine (TEA) (5.3 mL). Isopropyl isocyanate (1.87 mL) was added dropwise over 10 minutes and the whole mixture was stirred at 40±2° C. to complete dissolution. The mixture was cooled to room temperature and stirred for another 2 hours. The pH of the mixture was adjusted to 4.3 while increasing the temperature around 35° C. The mixture was cooled again to room temperature, filtered and washed with acetonitrile:water (1:1) mixture (10 mL). The wet crude product was triturated in acetonitrile:water mixture (5:1, 13 mL) at 60° C. for half an hour, filtered and washed with acetonitrile:water (5:1) mixture (2×7 mL). The triturated product was then dried under high vacuum (3 mm Hg) at 50° C. for 6 hours to get 5.4 g of crude torsemide (81.5% crude yield).

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed is:

1. A process for making a compound of the formula

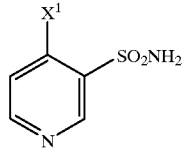

comprising the steps of:
(a) adding a compound of the formula

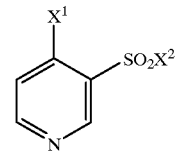

to an organic solvent to form a mixture;
(b) adding ammonia to the mixture in step (a); and
(c) isolating the compound of the formula

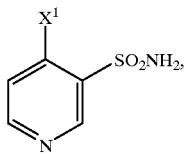

wherein $X^1$ and $X^2$ are each independently chloro, fluoro or bromo.

2. The process of claim 1 wherein $X^1$ and $X^2$ are both chloro.

3. The process of claim 1 wherein the organic solvent is selected from the group consisting of t-butyl-methyl ether, toluene, acetonitrile, methyl-isobutyl ketone, ethyl-methyl ketone, acetone, benzene, xylene, ethanol and isopropanol.

4. The process of claim 3 wherein the organic solvent is t-butyl-methyl ether.

5. The process of claim 1 wherein the ammonia is an aqueous solution.

6. The process of claim 1 wherein the ammonia is a gas.

7. A process for making (3-sulfonamide-4-chloro) pyridine comprising the steps of:
(a) adding (3-sulfonylchloride-4-chloro)pyridine to an organic solvent to form a mixture;
(b) adding ammonia to the mixture in step (a); and
(c) isolating (3-sulfonamide-4-chloro)pyridine.

8. The process of claim 7 wherein the organic solvent is selected from the group consisting of t-butyl-methyl ether, toluene, acetonitrile, methyl isobutyl ketone, ethyl methyl ketone, acetone, benzene, xylene, ethanol and isopropanol.

9. The process of claim 8 wherein the organic solvent is t-butyl methyl ether.

10. The process of claim 7 wherein the ammonia is added as an aqueous solution.

11. The process of claim 7, wherein the ammonia is a gas.

12. The process of claim 1 wherein the ammonia is added in an amount of about of about 1.75 to about 2.25 mole equivalents.

13. The process of claim 7 wherein the ammonia is added in an amount of about of about 1.75 to about 2.25 mole equivalents.

14. The process of claim 5, wherein the aqueous solution of ammonia is added drop-wise.

15. The process of claim 5, wherein the aqueous solution of ammonia is 25% ammonia hydroxide.

16. The process of claim 10, wherein the aqueous solution of ammonia is added drop-wise.

17. The process of claim 10, wherein the aqueous solution of ammonia is 25% ammonia hydroxide.

18. The process of claim 1, wherein the isolated compound of the formula

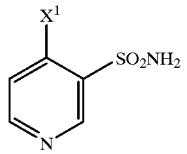

has a yield of at least about 74%.

19. The process of claim 1, wherein the isolated compound of the formula

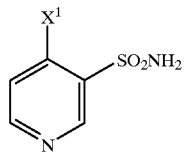

has a purity of at least about 93%.

20. The process of claim 7, wherein the isolated (3-sulfonamide-4-chloro)pyridine has a yield of at least about 74%.

21. The process of claim 7, wherein the isolated (3-sulfonamide-4-chloro)pyridine has a purity of at least about 93%.

* * * * *

UNITED STATES PATENT AND TRADEMARK OFFICE
CERTIFICATE OF CORRECTION

PATENT NO. : 6,635,765 B2
APPLICATION NO. : 09/812762
DATED : October 21, 2003
INVENTOR(S) : Marco Kordova It is certified that error appears in the above-identified patent and that said Letters Patent is hereby corrected as shown below:

Column 1, line 52, change "-sulfomamide-" to -- -sulfonamide- --

Column 2, line 30, change "-sulfomamide-" to -- -sulfonamide- --

Column 2, line 49, change "SAMOPY" to --SAMCPY--

Column 3, line 18, change "gives" to --give--

Column 3, line 18, change "uses" to --use--

Column 3, line 22, change "to s process" to --to a process--

Column 4, line 1, change "present intention" to --present invention--

Column 4, line 45, change "content of both are" to --content of both being--

Column 4, line 66, change "monitored by pH; which" to --monitored by pH; completion--

Column 5, line 5, change "(Scheme Il)" to --(Scheme II)--

Column 5, line 35, change "is" to --are--

Column 5, line 46, change "monitored by pH; which" to --monitored by pH; completion--

Column 5, line 66, change "is" to --are--

Column 6, line 22, change "sulfomamide" to --sulfonamide--

Column 6, line 29, change "sulfomamide" to --sulfonamide--

Column 6, line 64, change "sulfomamide" to --sulfonamide--

Column 7, line 33, change "allowed to increase to about 22 to abut 26° C.," to --allowed to increase to between about 22° C. and about 26° C.,--

Column 7, line 49, change "sulfomamide" to --sulfonamide--

UNITED STATES PATENT AND TRADEMARK OFFICE
CERTIFICATE OF CORRECTION

PATENT NO. : 6,635,765 B2
APPLICATION NO. : 09/812762
DATED : October 21, 2003
INVENTOR(S) : Marco Kordova It is certified that error appears in the above-identified patent and that said Letters Patent is hereby corrected as shown below:

Column 8, line 63, change "of about of about" to --of about--

Column 8, line 66, change "of about of about" to --of about--

Signed and Sealed this

Twenty-fifth Day of March, 2008

JON W. DUDAS
*Director of the United States Patent and Trademark Office*